(12) United States Patent
Kim et al.

(10) Patent No.: US 9,376,353 B2
(45) Date of Patent: Jun. 28, 2016

(54) METHOD OF PRODUCING AROMATIC HYDROCARBONS AND OLEFIN FROM HYDROCARBONACEOUS OILS COMPRISING LARGE AMOUNTS OF POLYCYCLIC AROMATIC COMPOUNDS

(71) Applicant: SK INNOVATION CO., LTD., Seoul (KR)

(72) Inventors: Cheol Joong Kim, Daejeon (KR); Sung Won Kim, Seoul, KS (US); Sang Hun Oh, Gyeonggi-do (KR); Il Yong Jeong, Seoul (KR); Kang Seok Go, Daejeon (KR); Sung Bum Park, Daejeon (KR); Dae Hyun Choo, Busan (KR); Hyuck Jae Lee, Daejeon (KR); Hong Chan Kim, Jeju-do (KR); Jae Suk Koh, Daejeon (KR); Yong Seung Kim, Seoul (KR); Gyung Rok Kim, Daejeon (KR); Myoung Han No, Daejeon (KR); Sun Choi, Daejeon (KR); Seung Hoon Oh, Seoul (KR); Tae Jin Kim, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 202 days.

(21) Appl. No.: 14/355,391

(22) PCT Filed: Oct. 31, 2012

(86) PCT No.: PCT/KR2012/009020
§ 371 (c)(1),
(2) Date: Apr. 30, 2014

(87) PCT Pub. No.: WO2013/066029
PCT Pub. Date: May 10, 2013

(65) Prior Publication Data
US 2014/0275671 A1     Sep. 18, 2014

(30) Foreign Application Priority Data

Nov. 1, 2011 (KR) ........................ 10-2011-0112862

(51) Int. Cl.
| | |
|---|---|
| *C07C 4/14* | (2006.01) |
| *C07C 4/18* | (2006.01) |
| *C07C 4/06* | (2006.01) |
| *C07C 5/05* | (2006.01) |
| *C07C 5/11* | (2006.01) |
| *C10G 69/04* | (2006.01) |
| *C10G 45/44* | (2006.01) |

(52) U.S. Cl.
CPC ... *C07C 5/11* (2013.01); *C07C 4/06* (2013.01); *C10G 45/44* (2013.01); *C10G 69/04* (2013.01); *C10G 2300/1096* (2013.01); *C10G 2400/20* (2013.01); *C10G 2400/30* (2013.01)

(58) Field of Classification Search
CPC .............. C07C 4/14; C07C 4/18; C07C 4/06; C07C 5/05
USPC .......................... 585/319, 468, 483, 484, 271
See application file for complete search history.

(56) References Cited

U.S. PATENT DOCUMENTS

| | | | |
|---|---|---|---|
| 2009/0314683 A1 | 12/2009 | Matsushita | |
| 2010/0331590 A1 | 12/2010 | Majumder et al. | |
| 2011/0207979 A1 | 8/2011 | Kim et al. | |
| 2013/0006027 A1* | 1/2013 | Yanagawa | .............. C10G 69/08 585/251 |

FOREIGN PATENT DOCUMENTS

| | | |
|---|---|---|
| EP | 1734098 A1 | 12/2006 |
| KR | 20100040309 A | 4/2010 |
| KR | 20100041802 A | 4/2010 |
| WO | 2009008876 A1 | 1/2009 |
| WO | 2009008878 A1 | 1/2009 |
| WO | 2011061576 A1 | 5/2011 |
| WO | 2011118753 A1 | 9/2011 |

OTHER PUBLICATIONS

European Search Report dated Jun. 22, 2015.
PCT/KR2012/009020, International Search Report and Written Opinion, Mar. 21, 2013 (6 pages).
CN2012800533630, Office Action, Dec. 1, 2014 (9 pages).

\* cited by examiner

*Primary Examiner* — Thuan D Dang
(74) *Attorney, Agent, or Firm* — Abelman, Frayne & Schwab

(57) ABSTRACT

This invention relates to a method of producing aromatic hydrocarbons and olefin from hydrocarbonaceous oils including large amounts of polycyclic aromatic compounds having two or more rings via partial hydrogenation in the presence of a hydrogenation catalyst and catalytic cracking in the presence of a catalytic cracking catalyst.

3 Claims, 1 Drawing Sheet

METHOD OF PRODUCING AROMATIC HYDROCARBONS AND OLEFIN FROM HYDROCARBONACEOUS OILS COMPRISING LARGE AMOUNTS OF POLYCYCLIC AROMATIC COMPOUNDS

CROSS-REFERNCE TO RELATED APPLICATIONS

This application is a National Phase of PCT/KR2012/009020, filed 31 Oct. 2012, which claims priority from Korean Application No. KR 10-2011-0112862, filed 1 Nov. 2011, each application being incorporated herein by reference.

TECHNICAL FIELD

The present invention relates to a method of producing aromatic hydrocarbons (e.g. benzene, toluene, xylene, aromatic hydrocarbons having at least nine carbons (hereinafter referred to as C9+ aromatic hydrocarbons), etc.) and olefin via partial hydrogenation and catalytic cracking from hydrocarbonaceous oils comprising large amounts of polycyclic aromatic compounds.

BACKGROUND ART

The demand for benzene, toluene, and xylene (BTX) is increased worldwide by 4~6% per year, which reaches a sharp increase of as much as two times GDP growth and about three times the demand growth for petroleum products. Such an increase is caused due to the rapidly increasing demand of aromatic hydrocarbons particularly in China.

Conventionally, benzene, toluene and xylene have been produced by hydrotreating and extracting pyrolysis gasoline obtained together with main feedstock products such as ethylene, propylene and so on in naphtha pyrolysis plants using naphtha, or by separating a reformate resulting from reforming naphtha.

However, such techniques for preparing aromatic hydrocarbons are problematic because only naphtha having a narrow boiling point obtained via atmospheric distillation of crude oil is used, making it impossible to cope with the shortage of naphtha in the world market due to the rapidly increasing demand of aromatic hydrocarbons. Hence, aromatic hydrocarbon feeds which can replace naphtha are required, and furthermore, increasing the yield of aromatic hydrocarbons and olefin is receiving great attention.

DISCLOSURE OF INVENTION

Technical Problem

Thorough research was carried out by the present inventors aiming to solve the problems encountered in the related art, and resulted in the finding that when hydrocarbonaceous oils including large amounts of polycyclic aromatic compounds having two or more rings are subjected to partial hydrogenation under special operating conditions and catalytic cracking, aromatic hydrocarbons (e.g. benzene, toluene, xylene, C9+ aromatic hydrocarbons, etc.) and olefin may be produced at high yield, and that the operating conditions for partial hydrogenation have an influence on catalytic cracking, which culminated in the present invention.

Accordingly, the present invention is intended to provide a method of producing benzene and C9+ aromatic hydrocarbons and olefin at high yield via partial hydrogenation and catalytic cracking using hydrocarbonaceous oils including large amounts of polycyclic aromatic compounds.

Solution to Problem

According to an embodiment of the present invention, a method of producing aromatic hydrocarbons and olefin is provided, which includes (a) subjecting an oil including a large amount of a polycyclic aromatic compound having two or more rings to partial hydrogenation under reaction conditions of 310~360° C., 50~70 atm, and a liquid hourly space velocity (LHSV) of 0.7~1.0 hr$^{-1}$ in the presence of a hydrogenation catalyst, thus obtaining a partially hydrogenated component, (b) subjecting the partially hydrogenated component obtained in (a) to catalytic cracking in the presence of a catalytic cracking catalyst, thus obtaining a catalytic cracked component, and (c) separating the catalytic cracked component obtained in (b) into (i) benzene, toluene, xylene and a C9+ aromatic hydrocarbon, (ii) an olefin component, and (iii) a residual oil.

In the embodiment of the invention, partial hydrogenation may be performed under the reaction conditions of 310~360° C., 50~70 atm, and LHSV of 0.7~1.0 hr$^{-1}$, particularly 340~360° C., 50~70 atm, and LHSV of 0.7~1.0 hr$^{-1}$, and more particularly 340~360° C., 55~65 atm, and LHSV of 0.7~1.0 hr$^{-1}$.

In the embodiment of the invention, the method may further include transalkylating the separated C9+ aromatic hydrocarbon. When transalkylation is performed in this way, it is not a cracking process and thus the production of olefin is not increased but the aromatic compound may be further converted into higher value-added aromatic compounds (e.g. benzene, xylene).

In the embodiment of the invention, the method may further include recycling the (iii) residual oil separated in (c) back to (a).

Advantageous Effects of Invention

According to the present invention, aromatic hydrocarbons such as benzene, toluene, and xylene, can be produced at high concentrations from hydrocarbonaceous oils comprising large amounts of polycyclic aromatic compounds having two or more rings, thus enabling mass production of high value-added aromatic hydrocarbons.

Also, among a variety of aromatic hydrocarbons and olefins, high value-added xylene and high value-added propylene can be selectively separated, so that byproducts which are comparatively worthless can be recovered and reprocessed to obtain high value-added xylene and propylene, thereby maximizing the added value thereof.

Also, according to the present invention, the consumption of expensive hydrogen is minimized and the rate of conversion of oils including aromatic compounds into BTX, C9+ aromatic hydrocarbons and olefin can be increased, thus reducing a recycle rate per unit feed.

BRIEF DESCRIPTION OF DRAWINGS

The above and other objects, features and advantages of the present invention will be more clearly understood from the following detailed description taken in conjunction with the accompanying drawings, in which.

BEST MODE FOR CARRYING OUT THE INVENTION

Figure 1:
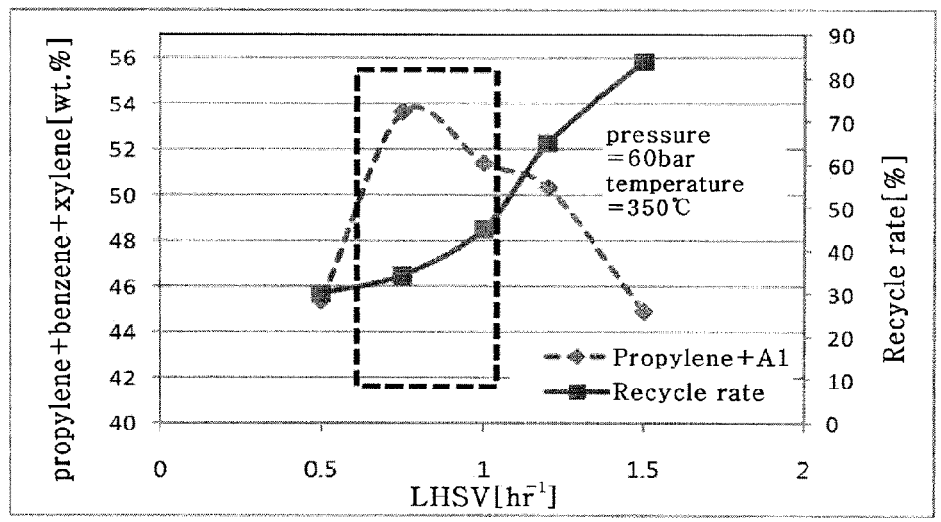
FIG. 1 is a graph illustrating the yield of propylene+benzene+xylene and the recycle rate depending on changes in LHSV in a partial hydrogenation process according to an embodiment of the present invention.

Hereinafter, a detailed description will be given of the present invention.

In the present invention, oils including aromatic compounds may be a feed including large amounts of polycyclic aromatic compounds having two or more rings, for example light cycle oils, which are mainly generated in a fluid catalytic cracking (FCC) process, but the present invention is not limited thereto. All oils including large amounts of polycyclic aromatic compounds having two or more rings resulting from refinery/petrochemical processes may be used. In oils including large amounts of polycyclic aromatic compounds having two or more rings, the amount of the aromatic compound component may be particularly 50 wt % or more, and more particularly 70 wt % or more. Examples of these oils may include, but are not limited to, raw pyrolysis gasoline (RPG), heavy raw pyrolysis gasoline (heavy RPG), heavy aromatics, atmospheric gas oil, FCC gasoline, light cracked naphtha, heavy cracked naphtha, FCC decanted oil, vacuum gas oil, coker gas oil, coker diesel, coker naphtha, heavy and reduced petroleum crude oil, petroleum atmospheric distillation bottom, petroleum vacuum distillation bottom, pitch, asphalt, bitumen, tar sand oil, shale oil, liquid products derived from coal liquefaction processes, heavy hydrocarbon residues, or mixtures thereof.

The aromatic hydrocarbons produced according to an embodiment of the invention may include benzene, toluene, and xylene, and the olefin may be ethylene, propylene, butylene, and naphthalene.

In the embodiment of the invention, partial hydrogenation means that an oil including a large amount of a polycyclic aromatic compound having two or more aromatic rings is hydrogenated in the presence of a hydrogenation catalyst so that an aromatic compound component having two or more aromatic rings is saturated into an aromatic component having one aromatic ring. As used herein, partial hydrogenation and partial saturation may be used interchangeably, and are regarded as having the same meaning.

In the embodiment of the invention, partial hydrogenation may be carried out in such a manner that all of two or more aromatic rings of an aromatic compound component are partially saturated except for one aromatic ring, or the saturated rings are isomerized. For example, naphthalene composed of two aromatic rings may be partially saturated into tetralin or may be isomerized into methyl indane. This is because the aromatic ring does not decompose under process conditions in the catalytic cracking process. In order to produce large amounts of high value-added benzene, toluene, xylene and/or propylene, it is important to adjust the extent of partial hydrogenation. The feed which is introduced into a catalytic cracking unit after partial hydrogenation may include a large amount of an aromatic hydrocarbon having one ring in which an aromatic compound having one ring and a long branch having one or more carbons are connected, and a small amount of an aromatic hydrocarbon having two or more rings, or an aromatic hydrocarbon in which all of hydrocarbons are saturated.

The case where the extent of partial hydrogenation is severe is problematic because all aromatic hydrocarbons having two or more rings are saturated, and are thus completely converted into paraffin or olefin in the catalytic cracking process. If the extent of partial hydrogenation is too low, a saturated cyclic hydrocarbon is turned back into an aromatic hydrocarbon having two or more rings due to dehydrogenation upon catalytic cracking, and thereby the conversion rate into a monocyclic aromatic hydrocarbon and an olefin is lowered and the recycle rate is increased. Furthermore, the volume of the reactor is increased, and hydrogen consumed to perform partial hydrogenation is discharged again as an exhaust gas that is worthless, undesirably resulting in inefficient use of hydrogen and very high hydrogen consumption relative to the yield. However, when partial hydrogenation is performed under reaction conditions according to the embodiment of the invention, the amount of the olefin is increased and the amount of the aromatic hydrocarbon having one ring is increased compared to the above partial hydrogenation, and the recycle rate is remarkably decreased.

According to the embodiment of the invention, among the two rings, one ring is saturated and then broken and converted into an olefin, and the other ring that is not saturated may be converted into BTX. In the embodiment of the invention, the catalyst used for partial hydrogenation may be provided in the form of not being supported, or in the form of a metal ingredient being supported on at least one support of alumina and silica. Also, the metal ingredient may include one or more selected from among metal elements of Groups 6, 9, and 10. Particularly, the metal ingredient may include one or more selected from among cobalt, molybdenum, nickel, and tungsten.

In the embodiment of the invention, the hydrogenation catalyst may be provided in the form of not being supported, or in the form of a metal ingredient being supported on a support such as an inorganic oxide or carbon. The inorganic oxide may be one or more selected from among silica, alumina, silica-alumina, zirconia, titania, aluminum phosphate, niobia, clay, and zeolite.

In the embodiment of the invention, the catalyst used in the hydrogenation may include one or more selected from among metal elements of Groups 6, 7, 8, 9, 10, and 11 of all 18 groups of the periodic table. For example, the metal ingredient may be one or more selected from among Cr, Mo, W, Ru, Co, Rh, Ni, Pd, Pt, Cu, and Fe. Also, the metal may be one or more selected from among Mo, W, Co, and Ni.

In the embodiment of the invention, the catalyst used in the hydrogenation may be NiMo, CoMo, or W.

Upon partial hydrogenation, not only partial saturation of the aromatic ring but also desulfurization and denitrification to remove impurities such as sulfides or nitrogen compounds from the oil may take place, and thus impurities may be easily removed from the oil even without additional removal of impurities.

In the embodiment of the invention, the feed introduced into the partial hydrogenation unit may include a light cycle oil including about 50 wt % or more of an aromatic compound. This is because the production of a final mono-ring or BTX is increased in proportion to an increase in the amount of the aromatic compound having two or more rings.

In the embodiment of the invention, the separated liquid aromatic hydrocarbon may be further separated into benzene, toluene, xylene, and C9+ aromatic hydrocarbons. To this end, a distillation process or the like may be applied and a variety of separation processes known in the art may be utilized.

In the embodiment of the invention, the catalytic cracking catalyst used for catalytic cracking may be a solid molding catalyst including one or more porous solid acids. The solid acid may include an amorphous solid acid such as silica, alumina or silica-alumina, or a crystalline zeolite molecular sieve having a molar ratio of Si/Al of 300 or less and a pore size of 4~10 Å (angstroms) or more.

The crystalline zeolite molecular sieve may be provided in the form of a combination of any one zeolite molecular sieve selected from among FAU, MOR, and BEA and having a large pore size of 6.5Å or more so as to react the aromatic component in pores, and any one zeolite molecular sieve selected from among MFI, MEL, and FER and having a medium pore size of 5~6.5Å. The weight ratio of the zeolite molecular sieve having a large pore size to the zeolite molecular sieve having a medium pore size is 5/95~95/5, and particularly 50/50~95/5. The catalytic cracking catalyst may be prepared by mixing 10~95 wt % of at least one zeolite molecular sieve selected from among FAU, MOR, and BEA with 5~90 wt % of an inorganic binder such as alumina or clay and spraying and drying the mixture to have a particle size of 10~300 μm.

In the embodiment of the invention, catalytic cracking in the presence of the catalytic cracking catalyst functions to break a naphthenic ring or a long branch having two or more carbons linked to an aromatic hydrocarbon having one or more aromatic rings. Upon partial hydrogenation, in an aromatic hydrocarbon having two or more aromatic rings, the aromatic rings other than one aromatic ring are partially saturated, and the bond of the naphthenic ring thus partially saturated is broken, thereby forming a high value-added aromatic component, or a C9+ aromatic hydrocarbon feed in the subsequent process.

In the case where catalytic cracking activity is too high, both a naphthenic ring or a long branch having two or more carbons and a short branch having one carbon are cut, so that the high value-added aromatic component is converted into a cheap component, and a monocyclic aromatic component is converted into coke which is thus regarded as worthless. In such a catalytic cracking procedure, because inevitable loss of some aromatic rings may occur, the reaction temperature should be set to 350~750° C. and the catalyst/oil ratio should be set to 3~15 so that undesired moieties are not decomposed, thus appropriately controlling the cracking activity.

In the embodiment of the invention, the product after catalytic cracking may be separated into (i) benzene, toluene, xylene and C9+ aromatic hydrocarbons, (ii) an olefin, and (iii) a residual oil. The separated (i) benzene, toluene, xylene and C9+ aromatic hydrocarbons may be recovered or may be subjected to additional transalkylation and thus converted into high value-added aromatic hydrocarbons. The (ii) high value-added light olefin including ethylene, propylene, butylene, etc. may be recovered. The (iii) residual oil may include, as unintended components, i) an aromatic component having two or more rings, ii) a monocyclic aromatic component which has a hydrocarbon group having five or more carbons and thus is not used as a high value-added aromatic product feed, iii) a monocyclic aromatic component which has a naphthenic ring and thus is not a high value-added product and is not used as a high value-added aromatic product feed, and iv) a component which is not a high value-added product and is not used as a high value-added aromatic product feed, other than the above components. The product after catalytic cracking may contain a large amount of naphthalenic compound. For example, methyl naphthalene, dimethyl naphthalene, or the like may be included. The naphthalenic compound may be recycled back to partial hydrogenation together with the residual oil. Also, it may be additionally separated and treated and thus be used for other purposes.

The present invention is described in more detail via the following examples which are not construed as limiting the scope of the invention.

As shown in Table 1 below, among fluid catalytic cracked oils, a light cycle oil having a boiling point of 170~360° C. was prepared as a feed. The light cycle oil of fluid catalytic cracking used in the embodiment of the invention may have different properties, compositions and yields of fluid catalytic cracked oils depending on the kind of fluid catalytic cracking feed and the operating conditions, and the claims of the invention are not limited thereby.

TABLE 1

| Items | Feed |
|---|---|
| Specific gravity (15/4° C.) | 0.9134 |
| Sulfur, wt ppm | 3.161 |
| Nitrogen, wt ppm | 324 |
| Aromatic, wt % | 78 |
| Distillation, D-86° C. | |
| IBP | 152.2 |
| 5% | 166.6 |
| 10% | 180.2 |
| 30% | 204.2 |
| 50% | 233.8 |
| 70% | 269.4 |
| 90% | 315.2 |
| 95% | 331.4 |
| EBP | 390.8 |

EXAMPLE 1 AND COMPARATIVE EXAMPLES 1 AND 2

The above feed was introduced into a partial hydrogenation unit. The partial hydrogenation was performed using a fixed bed reactor in the presence of a nickel-molybdenum combined hydrogenation catalyst. The reaction conditions for partial hydrogenation are given in Table 2 below.

TABLE 2

| Operating conditions | Ex. 1 | Comp. Ex. 1 | Comp. Ex. 2 |
|---|---|---|---|
| Catalyst | NiMo | NiMo | NiMo |
| Loading amount | 75 cc | 75 cc | 75 cc |
| Reaction pressure, kg/cm$^2$ | 60 | 60 | 80 |
| H$_2$/Oil, Nm$^3$/kl | 800 | 800 | 800 |
| LHSV, hr$^{-1}$ | 0.75 | 1.5 | 0.75 |
| Reaction temperature, ° C. | 350 | 300 | 350 |

After completion of the partial hydrogenation, the resulting feed was introduced into a fluid catalytic cracking reactor. The catalytic cracking catalyst was a commercially available Y-type zeolite-containing silica-alumina catalyst (49% of alumina, 33% of silica, 2% of a rare earth metal and a remainder of an inorganic binder). The reaction temperature was 549° C., and the reaction pressure was 25.3 psig, and the catalyst/oil ratio was 8, and WHSV was 27.2 hr$^{-1}$. A circulating fluidized bed catalytic reactor enabling the reaction of the catalyst and the continuous regeneration of the inactivated catalyst was used.

The operating conditions for fluid catalytic cracking and the single pass run results are given in Table 3 below.

TABLE 3

| Catalytic cracking conditions | Ex. 1 | Comp. Ex. 1 | Comp. Ex. 2 |
|---|---|---|---|
| $H_2$ consumption [per unit feed] | 1.56 | 1.45 | 2.49 |
| Conversion | 76.09 | 42.85 | 79.66 |
| Recycle rate | 23.91 | 57.15 | 20.34 |
| A1 + C3 = | 42.96 | 22.28 | 37.43 |
| [Detailed composition] | | | |
| Coke[1] | 3.42 | 6.76 | 1.52 |
| C1/2/2-/3[2] | 0.42 | 2.75 | 0.41 |
| C3=[3] | 6.34 | 3.73 | 9.80 |
| C4+[4] | 10.40 | 9.73 | 17.20 |
| N1[5] | 2.72 | 0.50 | 1.73 |
| N2[6] | 0.08 | 0.00 | 0.60 |
| A1[7] | 36.62 | 18.54 | 27.62 |
| A1N1[8] | 5.84 | 6.44 | 6.10 |
| A1N2[9] | 0.00 | 0.00 | 0.00 |
| A2[10] | 17.08 | 39.80 | 13.45 |
| A2N1[11] | 0.13 | 2.04 | 0.35 |
| A2N2[12] | 0.00 | 0.00 | 0.00 |
| A3[13] | 1.80 | 4.51 | 1.57 |
| Oxygenate[14] | 0.00 | 0.00 | 0.00 |
| Micell[15] | 2.11 | 5.03 | 4.22 |

(unit: wt %)

The abbreviations used in Table 3 are as follows.
1) Coke
2) C1/2/2-/3: methane, ethane, ethylene, propane
3) C3=: propylene
4) C4+: paraffin or olefin of butane or more (four or more carbons)
5) N1: a component having one naphthene ring
6) N2: a component having two naphthene rings
7) A1: a component having one benzene ring (e.g. tri-methyl benzene, etc.)
8) A1N1: a naphtheno-aromatic component such as tetralin in which a benzene ring having a naphthene ring attached thereto includes alkyl or the like
9) A1N2: a di-naphtheno-aromatic component in which one benzene ring having two naphthene rings attached thereto includes alkyl or the like
10) A2: a component having two benzene rings, such as naphthalene
11) A2N1: a component having two benzene rings having one naphthene ring attached thereto
12) A2N2: a component having two benzene rings having two naphthene rings attached thereto
13) A3: a component having three benzene rings, such as anthracene
14) Oxygenate: a component containing oxygen
15) Micell: components which were not completely separated in an analyzer As is apparent from Table 3, according to the present invention, the conversion rate was increased and the recycle rate was decreased, and the amounts of aromatic hydrocarbon having one ring and propylene resulting from partial hydrogenation and catalytic cracking were excessive.

As used herein, the conversion rate means the yield of a product other than a material having ten or more carbons including aromatics having two or more rings corresponding to the same appearance as that of the feed in the product after catalytic cracking, and the recycle rate is calculated from "100 conversion rate". Although the conversion rate of the process performance is regarded as important, the yield of BTX and propylene which are the desired products of the invention is very important. Furthermore, A1 is a precursor which will be converted into BTX, and thus the reaction performance may be determined by evaluating the yield of "A1+C3=".

In Comparative Example 1, the hydrocarbon partially hydrogenated to a low level was turned back into a component having two or more rings (feed) via dehydrogenation upon catalytic cracking, resulting in a decreased conversion rate and an increased recycle rate. Thus, A1+C3= was low. In Comparative Example 2 in which excessive hydrogenation was conducted, a large number of rings were saturated with hydrogen, and all of them were decomposed regardless of dehydrogenation upon catalytic cracking, and thus the component having two or more rings was comparatively low, resulting in a high conversion rate and a low recycle rate. However, because the aromatic component was decreased in the feed of the catalytic cracking due to excessive hydrogen saturation, the yield of the aromatics such as BTX was low, and thus A1+C3= became low. As seen in the above example, high A1+C3= could be obtained in the present invention.

Test Example 1 (Testing Effects of Lhsv Upon Partial Hydrogenation)

This test example was conducted under the same conditions as in Example 1, with the exception that LHSV was changed upon partial hydrogenation.

In Test Example 1, the unconverted portion was circulated thus obtaining the yield of propylene+benzene+xylene and the recycle rate.

The results of Test Example 1 are shown in FIG. 1. As shown in FIG. 1, when LHSV was in the range of 0.75~1.0 $hr^{-1}$, the yield of propylene+benzene+xylene was high and the recycle rate was low. If LHSV was 1.5 $hr^{-1}$ or more, the yield of propylene+benzene+xylene was decreased and the recycle rate was increased.

Test Example 2 (Testing Effects of Partial Pressure of Hydrogen Upon Partial Hydrogenation)

This test example was conducted under the same conditions as in Example 1, with the exception that partial pressure of hydrogen was changed upon partial hydrogenation.

In Test Example 2, the unconverted portion was circulated thus obtaining the yield of propylene+benzene+xylene and the recycle rate.

Figure 2:
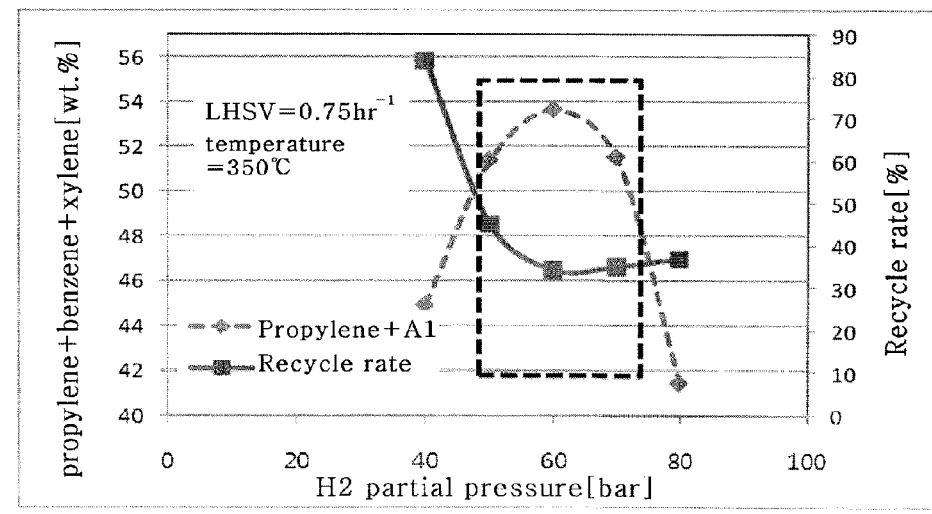
FIG. 2 is a graph illustrating the yield of propylene+benzene+xylene and the recycle rate depending on changes in partial pressure of hydrogen in a partial hydrogenation process according to an embodiment of the present invention.

The results of Test Example 2 are shown in FIG. 2. As shown in FIG. 2, when the partial pressure of hydrogen was in the range of 50~70 atm, the reaction performance was superior in consideration of both the yield of propylene+benzene+xylene and the recycle rate.

Test Example 3 (Testing Effects of Reaction Temperature Upon Partial Hydrogenation)

This test example was conducted under the same conditions as in Example 1, with the exception that the reaction temperature was changed upon partial hydrogenation.

In Test Example 3, the unconverted portion was circulated thus obtaining the yield of propylene+benzene+xylene and the recycle rate.

Figure 3:
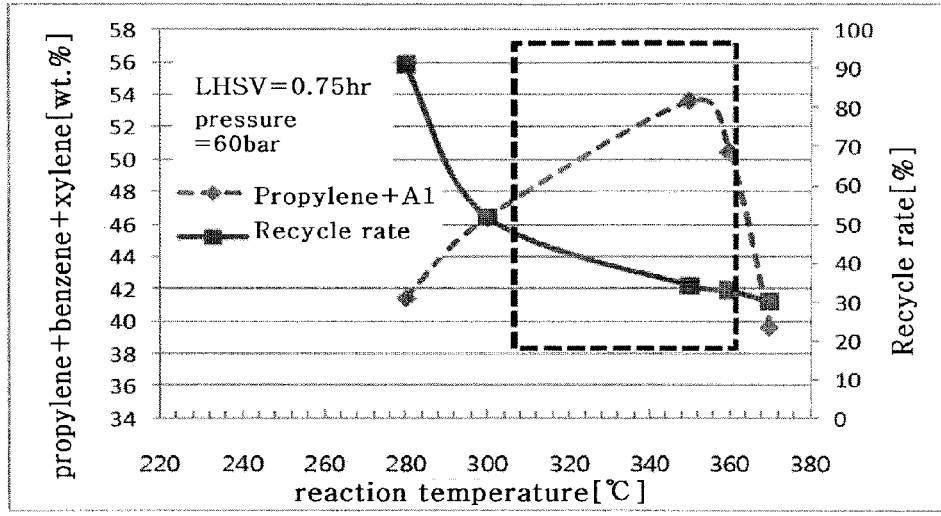
FIG. 3 is a graph illustrating the yield of propylene+benzene+xylene and the recycle rate depending on changes in reaction temperature in a partial hydrogenation process according to an embodiment of the present invention.

The results of Test Example 3 are shown in FIG. 3. As shown in FIG. 3, when the reaction temperature was as low as about 280° C., the recycle rate was very high and the yield of propylene+benzene+xylene was low. If the reaction temperature was higher than about 360° C., the recycle rate was low but the yield of propylene+benzene+xylene was low, which was evaluated to be inefficient.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of producing an aromatic hydrocarbon and an olefin, comprising:
   (a) subjecting an oil including a large amount of a polycyclic aromatic compound having two or more rings to partial hydrogenation under reaction conditions of 310~360° C., 50~70 atm, and LHSV (Liquid Hourly Space Velocity) of 0.7~1.0 hr$^{-1}$ using a hydrogenation catalyst, to obtaining a partially hydrogenated component with one aromatic ring;
   (b) subjecting the partially hydrogenated component obtained in (a) to catalytic cracking using a catalytic cracking catalyst, to obtain a catalytically cracked component, wherein the catalytic cracking catalyst is provided in the form of a combination of a zeolite molecular sieve having a large pore size of 6.5Å or more and a zeolite molecular sieve having a medium pore size of 5~6.5Å, and the weight ratio of the zeolite molecular sieve having a large pore size to the zeolite molecular sieve having a medium pore size is 5/95~95/5; and
   (c) separating the catalytic cracked component obtained in (b) into (i) benzene, toluene, xylene and a C9+ aromatic hydrocarbon, (ii) an olefin component, and (iii) a residual oil.

2. The method of claim 1, wherein (a) is performed under reaction conditions of 340~360° C., 55~65 atm, and LHSV of 0.7~1.0 hr$^{-1}$.

3. The method of claim 1, further comprising (d) recycling the (iii) residual oil separated in (c) back to (a).

* * * * *